| United States Patent [19] | [11] Patent Number: 4,639,517 |
| Reynes et al. | [45] Date of Patent: Jan. 27, 1987 |

[54] PROCESS FOR STABILIZING THIOCARBAMYLSULFENAMIDES

[75] Inventors: Enrique G. Reynes, Middleburg Heights; John O. Leising, Avon Lake, both of Ohio

[73] Assignee: The B F Goodrich Company, Akron, Ohio

[21] Appl. No.: 760,183

[22] Filed: Jul. 29, 1985

[51] Int. Cl.[4] .......................................... C07C 155/04
[52] U.S. Cl. ..................................... 544/85; 544/161; 564/75
[58] Field of Search ................... 564/75; 544/85, 106, 544/111, 131, 141, 161

[56] References Cited

U.S. PATENT DOCUMENTS 3,985,743 10/1976 Taylor .................................. 564/75

Primary Examiner—Christopher Henderson
Attorney, Agent, or Firm—J. Hughes Powell; Alan A. Csontos

[57] ABSTRACT

The stability, especially to heat, of thiocarbamylsulfenamides is improved when the thiocarbamylsulfenamide in solution is treated with acidic aqueous solutions. The recovered and dried thiocarbamylsulfenamides demonstrate improved resistance to heat and improved storage stability.

6 Claims, No Drawings

PROCESS FOR STABILIZING THIOCARBAMYLSULFENAMIDES

BACKGROUND OF THE INVENTION

Thiocarbamylsulfenamides are useful as accelerators for the sulfur vulcanization of unsaturated elastomers. The thiocarbamylsulfenamides are normally prepared by the reaction of a dithiocarbamate with an anime in the presence of an oxidizing agent. The resulting thiocarbamylsulfenamides, N,N'-[thiocarbonylthio]dimorpholine, for example, are normally not very storage stable, particularly under high temperature storage conditions that are often encountered under summer conditions or when exposed to other sources of heat. Under such conditions the thiocarbamylsulfenamide suffers degradation and a loss in activity. This results in slower cure rates and a decrease in scorch time.

A number of techniques to overcome this deficiency of the thiocarbamysulfenamides have been tried. Further processing of the thiocarbamysulfenamide with solvents and the like has been employed, but such processes are costly and have not been entirely satisfactory. Further, it would be desirable to eliminate having to handle a costly solvent and the subsequent processing steps, i.e., washing, filtration, drying, solvent recovery and purification and the like. Another approach has been by adding stabilizing materials to the thiocarbamylsulfenamides such as the oxirane compounds having molecular weights above 60 disclosed in U.S. Pat. No. 4,129,452 and the addition of certain acrylic amides and esters disclosed in U.S. Pat. No. 4,116,855. While this approach provided some stability to the thiocarbamylsulfenamides, the addition of these materials adds to the cost of the accelerator and introduces a foreign material in the thiocarbamylsulfenamide. Less expensive processes are still desirable that are incomplex.

SUMMARY OF THE INVENTION

The stability, especially to heat, of thiocarbamylsulfenamides is improved when the thiocarbamylsulfenamide in solution is treated with acidic aqueous solutions. The recovered and dried thiocarbamylsulfenamides demonstrate improved resistance to heat and improved storage stability.

DETAILED DESCRIPTION

Thiocarbamylsulfenamides can be prepared by the reaction of a dithiocarbamate metal salt and an amine with iodine in a potassium chloride solution or sodium hypochlorite as oxidizing agents. Another particularly useful method for preparing the thiocarbamylsulfenamides is described in U.S. Pat. No. 3,985,743 wherein an amine and a monohaloamine are reacted with carbon disulfide in the presence of a base. The thiocarbamylsulfenamides prepared by the process of this patent have the formula

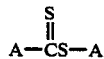

wherein A is selected from the group consisting of

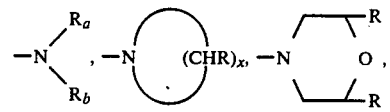

and mixtures thereof, where $R_a$ and $R_b$ are selected from the group consisting of hydrogen, an alkyl radical containing 1 to 24 carbon atoms, a cyanoalkyl radical containing 2 to 12 carbon atoms, an alkoxyalkyl radical containing 2 to 12 carbon atoms, an alkenyl radical containing 2 to 18 carbon atoms, all wherein the alkyl structure can contain secondary or tertiary carbon atom structures; a cycloalkyl radical containing 4 to 8 carbon atoms in the ring and additionally may have 1 to 4 carbon atoms alkyl substituents thereon; phenyl; an alkaryl or aralkyl radical containing 7 to 18 carbon atoms in the radical; and where R is hydrogen or an alkyl radical containing 1 to 2 carbon atoms and x=4 to 7.

Examples of such compounds are thiocarbamylsulfenamide and the derivatives thereof such as N,N-dimethyl thiocarbamylsulfenamide; N-methyl-N'-ethyl thiocarbamylsulfenamide; N,N,N',N'-tetramethyl thiocarbamylsulfenamide; N,N,N',N'-tetraethyl thiocarbamylsulfenamide; N,N,N',N'-tetrabutyl thiocarbamylsulfenamide; N-methyl-N',N'-diisopropyl thiocarbamylsulfenamide; N-octyl-N'-butyl thiocarbamylsulfenamide; N,N-didodecyl thiocarbamylsulfenamide; N,N-dioctadecyl thiocarbamylsulfenamide; N-isopropyl-N',N'-dicyclobutyl thiocarbamylsulfenamide; N-methyl-N-phenyl-N',N'-dimethyl carbamylsulfenamide; N,N-dimethyl-N'-tetramethylene carbamylsulfenamide; N'-oxydiethylene thiocarbamylsulfenamide; N,N-dimethyl-N'-oxydiethylene thiocarbamylsulfenamide; N,N-di-(α-cyanopropyl) thiocarbamylsulfenamide; N,N,N',N'-tetramethoxyethyl thiocarbamylsulfenamide; N,N-diallyl-N',N'-dimethyl thiocarbamylsulfenamide; N,N-dicyclohexyl-N'-N'-dibutyl thiocarbamylsulfenamide; N-cyclooctyl-N',N'-(1,3-dimethylhexyl) thiocarbamylsulfenamide; N-benzyl-N',N'-diethyl thiocarbamylsulfenamide; N-pentamethylene-N',N'-dipropyl thiocarbamylsulfenamide; N,N'-di-(tetramethylene) thiocarbamylsulfenamide; N,N'-di-(hexamethylene) thiocarbamylsulfenamide; N-pentamethylene-N'-oxydiethylene thiocarbamylsulfenamide; N-heptamethylene-N'-oxydiethylene thiocarbamylsulfenamide; N,N-di-(oxydiethylene) thiocarbamylsulfenamide; N-oxydiethylene-N'-2,6-dimethyloxydiethylene thiocarbamylsulfenamide; N,N'-di-(2,6-dimethyloxydiethylene) thiocarbamylsulfenamide; and N-2,6-dimethyloxydiethylene-N'-ethyl thiocarbamylsulfenamide.

The monohaloamines have the formula X-A, wherein X is —Cl, —Br, or —I, and A is defined as above. Examples of monohaloamines are monochloroamine, monobromoamine, methyl-chloramine, ethyl-chloroamine, ethyl iodoamine, t-butyl-chloroamine, hexyl-chloroamine, dodecyl-chloroamine, diemthyl-chloroamine, dimethyl-bromoamine, diethyl-chloroamine, ethyl-propyl-chloramine, diisopropyl-chloramine, ethyl-hexyl-chloroamine, diisopropyl-chloroamine, ethyl-hexyl-chloroamine, dioctyl-chloroamine, dioctyl-bromoamine, didodecyl-chloroamine, dioctadecyl-chloroamine, diallyl-chloroamine, α-cyanopropyl-chloroamine, di-methoxyethylchloroamine, phenyl-chloroamine, benzyl-chloroamine, benzyl-bromoamine, 3,5diethylbenzyl-chloroamine, cyclopentyl-chloroamine, cyclohexyl-chloroamine, dicyclobutyl-chloroamine, dicyclohexyl-bromoamine, tetramethyleneamine chloride, heptamethyleneamine chloride, hexamethyleneamine chloride, hexamethyleneamine iodide, 4-methyl-hexamethyleneamine chloride, oxydiethyleneamine chloride, 2,6-dimethyloxydiethyleneamine chloride, and the like.

The monochloroamines are preferred. They are readily prepared by reacting a primary or secondary amine with a chlorinating agent such as sodium hydrochlorite, NaOCl. This can be done in situ prior to the reaction of the amine and the chloroamine with the carbon disulfide. It is to be understood that monobromoamines and monoiodoamines may also be used.

Even more preferred are those monochloramines wherein when A is $-NR_aR_b$, $R_a$ is hydrogen or the same as $R_b$, and $R_b$ is an alkyl radical containing 1 to 24 carbon atoms or a cycloalkyl radical containing 4 to 8 carbon atoms in the ring, and when A is

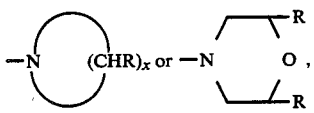

x is 4 to 7, and R is hydrogen or a methyl radical. Examples of such compounds are methyl-chloroamine, ethyl-chloroamine, t-butyl-chloroamine, hexyl-chloroamine, dimethyl-chloroamine, diethyl-chloroamine, ethyl-propyl-chloroamine, diisopropyl-chloroamine, disecbutyl-chloroamine, dihexyl-chloroamine, hexyl-octyl-chloroamine, diisooctyl-chloroamine, didecyl-chloroamine, methyl-dodecyl-chloroamine, ditetradecyl-chloroamine, dioctadecyl-chloroamine, cyclobutyl-chloroamine, cyclohexyl-chloroamine, dicyclopentyl-chloroamine, dicyclohexylchloroamine, di-(4-methyl-cyclohexyl)-chloroamine, tetramethyleneamine-chloroamine, pentamethyleneamine-chloride, 2,6-dimethyloxydiethyleneamine chloride, and the like.

The amines have the formula H-A, wherein A is defined as above. Examples of such amines would be those broadly disclosed haloamines as listed above except for the replacement of the chlorine atom with a hydrogen atom. More preferred are those amines wherein, when A is $-NR_aR_b$ is hydrogen or the same as $R_b$ and $R_b$ is an alkyl radical containing 1 to 24 carbon atoms; and when A is

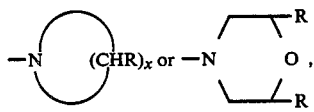

wherein x=4 to 7, and R is hydrogen or a methyl radical. Examples of the more preferred amines are methylamine, ethylamine, n-butylamine, hexylamine, dodecylamine, dimethylamine, diethylamine, ethylpropylamine, dibutylamine, dihexylamine, dioactylamine, didoceylamine, dioactadecylamine, tetramethylamine, pentamethylamine, hexamethyleneamine, oxydiethyleneamine, 2,6-dimethyloxydiethyleneamine, and the like.

The base can be an alkali metal hydroxide such as sodium hydroxide, potassium hydroxide, and the like; an alkali metal alcoholate wherein the alcohol is an aliphatic alcohol containing 1 to 10 carbon atoms such as sodium methoxide, sodium ethoxide, potassium butoxide, and the like; or the allkali metal salt of a weak acid such as organic acids containing 1 to about 8 carbon atoms including acetic acid, citric acid, benzoic acid and salicyclic acid; boric acid, phosphoric acid, carbonic acid, and the like. Examples of alkali metal salts of weak acids are sodium acetate, potassium benzoate, sodium borate, sodium phosphate, sodium carbonate, and the like. Excellent results were obtained when using an alkali metal hydroxide such as sodium hydroxide as the base.

The reactions can be conducted as a slurry in water but a more preferred variation is to conduct the reactions in an aqueous/non-aqueous medium. In this manner, higher yields and more pure products can be obtained. The medium consists of water and an organic solvent, preferably a chlorinated organic solvent such as methylene chloride, carbon tetrachloride, chloroform, ethylenedichloride, 1,1,1-trichloroethane, 1,1,2-trichloroethane, chlorobenzene, 1,1,2-trichloro, trifluoroethane and the like. The monochloroamine, the carbon disulfide and the thiocarbamylsulfenamide are all soluble in the non-aqueous or organic phase.

The temperature of the reactions ranges from near the freezing point of the mixture, about $-20°$ C., to near the boiling point of the mixture, about 80° to 100° C. A more preferred range is from about $-10°$ C. to about 40° C. Reaction times are from about 0.2 hours to about 2 hours.

The amine and the monochloroamine can both be used in a molar excess of the amount of the carbon disulfide present. However, yields of over 50% and in excess of 90% based on the theoretical yield are readily obtained using about 1 mol of monochloroamine and 1 mol of amine to every 1 mol of carbon disulfide present. By-products of the reaction include sodium chloride and water when sodium hydroxide is used.

The reactions are conducted with agitation. After the reactions, the mixture is allowed to separate and the non-aqueous or organic phase containing the thiocarbamylsulfenamide is separated from the aqueous layer. The thiocarbamylsulfenamides are usually crystalline materials but some are liquids at room temperatures. The products can be dissolved in an alcohol such as methanol and ethanol or in an alkane such as hexane, and then precipitated out by cooling. Yields after recrystallization are from about 50% to about 90% by weight of the theoretical yield.

While any acid may used to treat the organic phase containing the thiocarbamylsulfenamides in accordance with this invention, the stronger more highly ionized inorganic acids are preferred. Acids that can be used include acetic, formic, chloroactic, trichloroacetic and like organic acids, but they are expensive and larger amounts may be required to obtain the advantages of the invention. Therefore the inorganic acids normally are preferred such as hydrochloric acid, sulfuric acid, nitric acid, and the like. The acids are employed in dilute solutions in water and the concentration is not critical. Concentrations of about 0.1 to about 1.0 weight percent or more of acid at about 0.03N to about 0.2N have been used. Another basis is an amount of acid from about 0.1 to about 0.7 milliequivalents of acid per gram of thiocarbamylsulfenamide reaction solids. It is necessary that the amount of acid used is sufficient to reduce pH of the water phase in contact with the organic phase or solution containing the thiocarbamylsulfenamide from about 1 to at least less than about 5, and more preferably from a pH of about 2 to 4.

In the practice of the invention, after the reaction to form the desired thiocarbamylsulfenamide, the water phase and the organic phase containing the thiocarbamylsulfenamide, are allowed to separate, or are separated. The water phase may be removed from the reactor and the organic phase is treated with acid in the reactor. Or, the organic phase may be removed from the reaction vessel to another vessel and treated with the acid.

The organic phase is mixed with the aqueous acid with agitation to insure the reaction of acid with the impurities. While mixing times of about 15 minutes have been found to be satisfactory, less or longer times may be used. Longer times tie up the equipment and the time of contact with the acid only need be that required to lower the $\Delta T$ of the thiocarbamylsulfenamide. $\Delta T$ is the difference in the unaged thiocarbamylsulfenamide melting point and the melting point after aging in an air oven at 100° C. for 60 minutes. A $\Delta T$ of less than 3, and preferably less than 2, is desirable.

After the acid treatment the organic phase is washed with water. Normally 2 to 3 washes are sufficient. The water and organic solution are separated and the thiocarbamylsulfenamide recovered from the organic phase by removing the methylene chloride and drying the thiocarbamylsulfenamide at 20°–25° C. for 2 to 8 hours. This may be accomplished in a thin film dryer, by distillation, flashing, and the like, as is well known to those skilled in the art.

The following examples demonstrate the practice of the invention.

EXAMPLE I

In this example, a methylene chloride solution of N-oxydiethylenethiocarbamyl-N'-oxydiethylenesulfenamide was prepared by reacting morpholine, dissolved in methylene chloride, sequentially with a NaOCl bleach solution and carbon disulfide in the manner described in U.S. Pat. No. 3,985,743. At the end of the reaction the methylene chloride organic phase was separated from the water phase. The methylene chloride solution was diluted with methylene chloride to a total solids content of 12 percent. 100 volumes of this organic solution containing the N-oxydiethylenethiocarbamyl-N'-oxydiethylenesulfenamide was stirred with 100 volumes of hydrochloric acid having a normality of 0.06 N, the HCl being used in amount of 5.8 milliequivalents of acid based on 15.7 grams of solids. The aqueous acid and organic solutions were stirred together for about 15 minutes to a pH of the mixture of 2.7. The acid phase was separated from the organic solution by transferring the mixture to a separating vessel settling the layers, and decanting. The organic solution was then washed twice with 100 volumes of distilled water and separated from the water. The methylene chloride was then flashed off and the dried N-oxydiethylenecarbamyl-N'-oxydiethylenesulfenamide collected. The melting point of the N-oxydiethylenecarbamyl-N'-oxydiethylenesulfenamide was found to be 134.8° C. A sample of N-oxydiethylenecarbamyl-N'-oxydiethylenesulfenamide was aged in an air over at 100° C. for 60 minutes to test for stability. The melting point after aging was determined and found to be 133.0° C., for a $\Delta T$ of 1.8, this sample being very stable. When a control run was made without the acid wash, using only water washes, the unaged melting point was found to be 134.4° C. and the aged melting point was found to be 128.4°, for a $\Delta T$ of 6.0, which represents a very unstable product with unsatisfactory storage stability and product activity.

EXAMPLE II

In this series of runs, the procedure of Example I was repeated except that sulfuric acid, 0.09 to 0.16N, was substituted for the acetic acid. The Table below sets forth the varying conditions as to milliequivalents, Meq, of acid used, volumes of acid, the treatment time for the acid wash, pH of the acid-solution mixture, and the resulting unaged and aged melting points. The total solids in the organic solution was 27.4 grams.

TABLE I

| Run No. | 1 | 2 | 3 | 4 |
|---|---|---|---|---|
| Meq of $H_2SO_4$ | 0 | 5 | 7 | 9 |
| Vol. $H_2SO_4$-ml | 0 | 55 | 55 | 55 |
| Con. of Acid, Normality | — | 0.09 | 0.13 | 0.16 |
| Time-minutes | 30 | 30 | 40 | 30 |
| pH | 8.3 | 4.1 | 4.0 | 2.9 |
| Melting Point °C. | | | | |
| Unaged | 135.4 | 135.4 | 134.2 | 134.6 |
| Aged | 130.0 | 133.6 | 132.6 | 133.4 |
| $\Delta T$ | 5.4 | 1.8 | 1.6 | 1.2 |
| Stability | unstable | stable | stable | stable |

EXAMPLE III

The sulfuric acid of Example II was substituted with N-hydrochloric acid in this Example, otherwise the procedure of the previous Example was followed. Two undesirable impurities in N-oxydiethylenecarbamyl-N'-oxydiethylenesulfenamide are dimorpholine thiourea (DMTU) and 4(4'-morpholinodithio)thiomethyl morpholine. The amounts of these present, and a showing of the decrease in these two materials after the acid treatment is shown in Table II. The total solids in the organic phase was held constant in 13.8 grams.

TABLE II

| Run No. | 1 | 3 |
|---|---|---|
| Meq of HCl | 0 | 5.7 |
| Vol. HCl-ml | 0 | 100 |
| Conc., Acid Normality | — | 0.06 |
| pH | 8.1 | 2.3 |
| Melting Point °C. | | |
| Unaged | 135.2 | 134.2 |
| Aged | 130.0 | 133.0 |
| $\Delta T$ | 5.2 | 1.2 |
| Stability | unstable | stable |
| DMTU-% | 1.0 | 0.65 |
| CDS-% | 1.0 | 0.54 |

We claim:

1. A method for improving the heat stability of thiocarbamylsulfenamides comprising treating a thiocarbamylsulfenamide dissolved in an organic solvent with a dilute aqueous acid solution, to a pH of about 1 to less than about 5, separating the organic solution from the aqueous phase, removing the solvent from the thiocarbamylsulfenamide and drying.

2. A method of claim 1 wherein the thiocarbamylsulfenamide is N-oxydiethylenecarbamyl-N'-oxydiethylenesulfenamide, the solvent is a chlorinated organic liquid, and the acid is a highly ionized inorganic acid used in amount from about 0.1 to about 0.7 milliequivalents of acid per gram of thicarbamylsulfenamide reaction solids.

3. A method of claim 2 wherein the solvent is methylene chloride, and the inorganic acid is hydrochloric acid of about 0.03N to about 0.2N, in concentrations of about 0.1 to about 1.0 weight percent.

4. A method of claim 2 wherein the solvent is methylene chloride, and the inorganic acid is sulfuric acid of about 0.03N to about 0.2N, in concentrations of about 0.1 to about 1.0 weight percent.

5. A method of claim 3 wherein an amount of hydrochloric acid is added in a 0.1 to 0.4 weight percent solution in water to reduce the pH of the mixture of acid and methylene chloride solution to less than 3.

6. A method of claim 3 wherein an amount of sulfuric acid is added in a 0.4 to 1.0 weight percent solution in water to reduce the pH of the mixture of acid and methylene chloride solution to less than 4.

* * * * *